United States Patent
Liu et al.

(10) Patent No.: US 10,709,783 B2
(45) Date of Patent: *Jul. 14, 2020

(54) NEUTRON CAPTURE THERAPY SYSTEM FOR ELIMINATING AMYLOID β-PROTEIN

(71) Applicant: NEUBORON MEDTECH LTD., Nanjing, Jiangsu (CN)

(72) Inventors: Yuan-hao Liu, Jiangsu (CN); Jing He, Jiangsu (CN); Jui-fen Chen, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 138 days.

This patent is subject to a terminal disclaimer.

(21) Appl. No.: 16/010,818

(22) Filed: Jun. 18, 2018

(65) Prior Publication Data

US 2018/0360963 A1    Dec. 20, 2018

Related U.S. Application Data

(63) Continuation of application No. PCT/CN2016/111811, filed on Dec. 23, 2016.

(30) Foreign Application Priority Data

Dec. 30, 2015    (CN) .......................... 2015 1 1018353

(51) Int. Cl.
| | |
|---|---|
| *A61K 51/00* | (2006.01) |
| *A61M 36/14* | (2006.01) |
| *A61K 41/00* | (2020.01) |
| *A61N 5/10* | (2006.01) |
| *A61K 51/04* | (2006.01) |
| *C07F 5/02* | (2006.01) |
| *A61K 49/00* | (2006.01) |

(52) U.S. Cl.
CPC ...... *A61K 41/0095* (2013.01); *A61K 51/0453* (2013.01); *A61N 5/10* (2013.01); *A61N 5/1077* (2013.01); *C07F 5/025* (2013.01); *A61K 49/0008* (2013.01); *A61N 2005/109* (2013.01); *A61N 2005/1021* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 5,630,786 | A | 5/1997 | Griffin et al. |
| 10,239,895 | B2 * | 3/2019 | Liu ................ G01N 33/68 |
| 2009/0221512 | A1 | 9/2009 | Acosta et al. |
| 2010/0028967 | A1 | 2/2010 | Nishikawa et al. |
| 2010/0183513 | A1 | 7/2010 | Froestl et al. |
| 2011/0230415 | A1 | 9/2011 | Berlanga Acosta et al. |
| 2012/0309791 | A1 | 12/2012 | Froestl et al. |
| 2014/0341812 | A1 | 11/2014 | Cai et al. |
| 2016/0101198 | A1 | 4/2016 | Gonzales et al. |
| 2016/0158578 | A1 | 6/2016 | Liu et al. |

FOREIGN PATENT DOCUMENTS

| | | |
|---|---|---|
| CN | 101426517 A | 5/2009 |
| CN | 103127530 A | 6/2013 |
| CN | 105658244 A | 6/2016 |
| EP | 2612692 A1 | 8/2011 |
| WO | 2006027877 A1 | 3/2006 |

OTHER PUBLICATIONS

Kim et al. (J. Med. Chem. 2013, 56, 8104-8111).*
Gilbert et al. (Journal of Alloys and Compounds 2001, 328, 8-13).*
Cui et al. (Bioorg. Med. Chem. 2010, 18, 2777-2784).*
International Search Report of PCT/CN2016/111811, dated Mar. 3, 2017.

* cited by examiner

*Primary Examiner* — Michael G. Hartley
*Assistant Examiner* — Melissa J Perreira
(74) *Attorney, Agent, or Firm* — Locke Lord LLP; Tim Tingkang Xia, Esq.

(57) ABSTRACT

A neutron capture therapy system capable of eliminating amyloid β-protein includes a neutron capture therapy device and a compound capable of specifically binding to the amyloid β-protein having a nuclide with a large thermal neutron capture cross section. The neutron capture therapy device includes a neutron source, a beam shaping assembly and a collimator, the neutrons released by the neutron source pass through the beam shaping assembly and are slowed into a neutron beam within a certain energy range. The neutron beam irradiates the compound, and the energy generated by the reaction thereof can destroy the structure of the amyloid β-protein. The neutron capture therapy system can specifically eliminate the amyloid β-protein, and reduce the damage to the tissues surrounding the amyloid β-protein.

9 Claims, 4 Drawing Sheets

Graph A

Graph B

NEUTRON CAPTURE THERAPY SYSTEM FOR ELIMINATING AMYLOID β-PROTEIN

RELATED APPLICATION INFORMATION

This application is a continuation of International Application No. PCT/CN2016/111811, filed on Dec. 23, 2016, which claims priority to Chinese Patent Application No. 201511018353.5, filed on Dec. 30, 2015, the disclosures of which are hereby incorporated by reference.

FIELD OF THE DISCLOSURE

The present disclosure relates generally to a neutron capture therapy system, and, more particularly, to a neutron capture therapy system for eliminating amyloid β-protein.

BACKGROUND OF THE DISCLOSURE

Alzheimer's disease (usually abbreviated as AD) is the most common dementia among the elderly. Its histopathological manifestations are mainly senile plaques, neurofibrillary entanglement, and the death of regional neurons caused by apoptosis and so on.

Studies have shown that abnormal deposition of amyloid β-protein (usually abbreviated as Aβ) is one of the main pathogenesis of Alzheimer's disease. Amyloid β-protein is a polypeptide containing 39 to 43 amino acids produced by proteolytic action of amyloid precursor protein (APP) by β and γ secretase. Commonly in the human body is a peptide containing 40 ($A\beta_{1-40}$) or 42 ($A\beta_{1-42}$) amino acids, wherein $A\beta_{1-42}$ has a stronger toxicity, easier to accumulate into the core of amyloid β-protein deposition plaque, and the amyloid β-protein deposition plaque formed the deposition of amyloid β-protein can cause neurotoxicity. In normal physiological conditions, amyloid β-protein can be detected in both blood and cerebrospinal fluid, suggesting that amyloid β-protein itself does not cause Alzheimer's disease, whereas the deposition of amyloid β-protein is one of the causes of Alzheimer's disease.

Studies have shown that a large number of amyloid β-protein deposition plaques have accumulated in the hippocampus and cortical regions of the brain of patients with Alzheimer's disease, and reducing the amount of amyloid β-protein in the brain can delay or relieve the symptoms of Alzheimer's disease.

Amyloid β-protein can be degraded by a variety of peptidases, such as insulin-degrading enzymes (IDE) and neutral endopeptidase (NEP), both of which are zinc-dependent endoproteases. Studies have shown that in the presence of IDE and NEP, amyloid β-protein will be significantly reduced, but in the absence of IDE and NEP, how to destroy the structure of amyloid β-protein and reduce the accumulation of amyloid β-protein become one of the means to study the pathogenesis of Alzheimer's disease and even the treatment of Alzheimer's disease, and there is currently no way to effectively destroy the structure of amyloid β-protein.

SUMMARY

In order to be able to destroy the structure of amyloid β-protein, and eliminate amyloid β-protein, an aspect of the present disclosure provides a neutron capture therapy system for eliminating amyloid β-protein, including a neutron capture therapy device and a compound for specifically binding to the amyloid β-protein, wherein the compound contains a nuclide with a large thermal neutron capture cross section; and wherein the energy generated by the action of a neutron beam generated by the neutron capture therapy device on the nuclide of the compound destroys the structure of the amyloid β-protein, so as to achieve the purpose of eliminating these pathogenic proteins.

Implementations of this aspect may include one or more of the following features.

In practice, the beam generated by the neutron capture therapy device is a mixed beam including neutron rays, gamma rays and other radiations, however, it is the neutron beam in the mixed beam that is used in the process of using the beam to eliminate amyloid β-protein. The nuclides with a large thermal neutron capture cross section may include, but are not limited to $^{10}B$, $^{155}Gd$ or $^{157}Gd$. Wherein the nuclide with a large thermal neutron capture cross section refers to a nuclide having a neutron capture cross section greater than or equal to 100 times of the neutron capture cross section of the basic constituent elements (C, H, O, N, P, S) of the human body under the same energy of thermal neutron irradiation. Wherein H has the largest neutron capture cross section among the basic constituent elements of the human body under the same energy of thermal neutron irradiation. Under the condition of thermal neutron energy of 0.025 eV, the thermal neutron capture cross section of H is 0.2 barn, the thermal neutron capture cross section of $^{10}B$ is 3800 barn, the thermal neutron capture cross section of $^{155}Gd$ is 60700 barn, and the thermal neutron capture cross section of $^{157}Gd$ is 254000 barn, all are greater than 100 times of the thermal neutron capture cross section of the H element under the same energy of thermal neutron irradiation.

This kind of nuclides with a large thermal neutron capture cross section may react with the thermal neutrons to release at least one type of lethal ray that has a short range and essentially only destroys the structure of the amyloid β-protein that specifically binds to the compound without destroying other normal tissue, thus the harm to normal tissue is very little.

Preferably, in the neutron capture therapy system for eliminating amyloid β-protein, the nuclide with a large thermal neutron capture cross section is elected from the group consisting of $^{10}B$, $^{155}Gd$, and $^{157}Gd$.

The nuclide $^{10}B$, which has a large thermal neutron capture cross section, undergoes the following reaction under the irradiation of the neutron beam:

Reaction Formula I

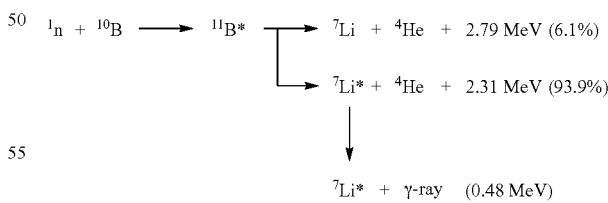

Two heavy particles of $^4He$ and $^7Li$ are generated by $^{10}B(n,\alpha)$ $^7Li$ neutron capture and nuclear splitting reaction, utilizing the characteristics of boron-containing ($^{10}B$) compound with a large thermal neutron capture cross section. As shown in Reaction Formula I, the average energy of the two heavy particles is about 2.33 MeV, with characteristics of high linearity transfer (LET), and short range. The linear energy transfer and range of α particles is 150 keV/μm, 8 μm, respectively, while that of $^7Li$ heavy particles is 175 keV/μm, 5 μm. The total range of the two particles is equivalent to about the size of one cell, so the radiation damage to the organism is limited to the cell level. When the boron-containing compound specifically binds to the amyloid β-protein, with the appropriate neutron source, the purpose of local destruction of amyloid β-protein can be achieved under the premise that it does not cause too much damage to the normal organization.

In the neutron capture therapy system for eliminating amyloid β-protein, it is preferred that the neutron capture therapy device includes a neutron source for generating a neutron beam, a beam shaping assembly located at the rear of the neutron source for shifting fast neutrons in the neutron beam with a wider spectrum generated by the neutron source to epithermal neutrons or thermal neutrons and a collimator located at the rear of the beam shaping assembly for converging the epithermal neutrons or the thermal neutrons. Generally, a fast neutron is defined as a neutron with energy range of great than 40 keV, epithermal neutron with energy range of 0.5 eV to 40 keV, and thermal neutron with energy range of less than 0.5 keV. A collimator with appropriate caliber is used for different sizes of amyloid β-protein deposition plaques.

Preferably, in the neutron capture therapy system for eliminating amyloid β-protein, the neutron source is an accelerator-based neutron source or a reactor-based neutron source.

Wherein the accelerator neutron source bombards an appropriate target (e.g., a lithium target or a beryllium target) by accelerating charged particles (such as proton beams) to produce neutrons by nuclear reaction, the most commonly used nuclear reactions are (d, n), (p, n) and (γ, n), etc.

The reactor neutron source utilizes atomic nucleus fission reactors to produce large amounts of neutrons, such neutron source is the strongest thermal neutron source. The neutrons can be lead out with an opening on the reactor wall, and the resulting neutron energy is continuously distributed, very close to the Maxwell distribution. Neutron beams with varying energies can be obtained by taking certain measures.

Preferably, in the neutron capture therapy system for eliminating amyloid β-protein, the beam shaping assembly includes a reflector and a moderator, wherein the reflector surrounds the moderator for reflecting neutrons diffused outside the beam shaping assembly back into the moderator, and the moderator is used to moderate fast neutrons into epithermal neutrons or thermal neutrons. Wherein the reflector is made of at least one of Pb or Ni; The material of the moderator may be composed of one or more of $Al_2O_3$, $BaF_2$, $CaF_2$, $CF_2$, $PbF_2$, $PbF_4$ and $D_2O$, or may be composed of the above-mentioned material of the moderator added with a lithium-containing substance, such as LiF and $Li_2CO_3$ containing $^6Li$.

Further, the beam shaping assembly includes a thermal neutron absorber and a radiation shield, wherein the thermal neutron absorber is made of $^6Li$ and the radiation shield includes a photon shield made of Pb and a neutron shield made of PE.

The thermal neutron absorber is adjacent to the moderator and is used to absorb the thermal neutrons to avoid excessive doses to the superficial normal tissue when treated; the radiation shield includes a photon shield made of Pb and a neutron shield made of PE for shielding the leaking neutrons or photons to reduce the normal tissue dose of the non-irradiated region, where the photon shield can be integrated with the reflector, and the neutron shield may be disposed at a position near the beam exit in the beam shaping assembly.

Preferably, in the neutron capture therapy system for eliminating amyloid β-protein, the compound capable of specifically binding to the amyloid β-protein has the structure of formula I:

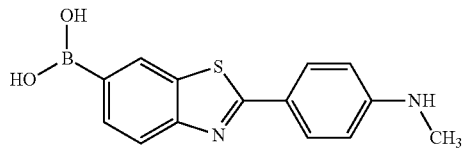

formula I

The compound of formula I is 6-borono-2-(4-methylaminophenyl)benzothiazole, wherein B in the $B(OH)_2$-group of the compound is $^{10}B$; the nuclide $^{10}B$ has abundance of 19.2% in nature. In the practical application of the compound for eliminating amyloid β-protein, the boron element in $B(OH)_2$-in 6-borono-2-(4-methylaminophenyl)benzothiazole may be $^{10}B$ or $^{11}B$, wherein the content of the compound containing the element $^{10}B$ is determined depending on the actual requirements.

The element C in the methylamine group of 6-borono-2-(4-methylaminophenyl)benzothiazole, is $^{12}C$ or $^{11}C$. The 6-borono-2-(4-methylaminophenyl)benzothiazole having $^{11}C$ can be used to determine the site of amyloid β-protein in the brain as imaging agent for PET, in addition to be used in the elimination of amyloid β-protein in a neutron capture therapy system.

The compound of formula I plays an intermediate role in the neutron capture therapy system for eliminating amyloid β-protein. In the neutron capture therapy system, $^{10}B$ on the compound of formula I is capable of capturing the neutrons emitted by the neutron capture therapy device and carrying out nuclear reactions to generate energy, which is capable of destroying the structure of the amyloid β-protein that specifically binds to the compound of formula I, thereby reducing the amyloid β-protein content. Since the compound of formula I is specifically bound to the amyloid β-protein and $^{10}B$ on the compound is capable of capturing thermal neutrons, thereby enabling the neutron capture therapy system to eliminate amyloid β-protein with high efficiency and targeting ability.

Wherein, in the neutron capture therapy system for eliminating amyloid β-protein, the compound of formula I is prepared from a compound of formula II:

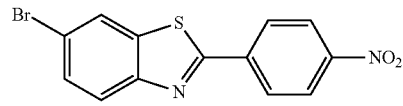

formula II

Preferably, the process for preparing the compound of formula I from the compound of formula II comprises steps of:

reducing the compound of formula II to obtain 6-bromo-2-(4-aminophenyl)benzothiazole;

reacting 6-bromo-2-(4-aminophenyl)benzothiazole and formaldehyde to obtain 6-bromo-2-(4-methylaminophenyl) benzothiazole;

reacting 6-bromo-2-(4-methylaminophenyl)benzothiazole and bis(pinacolato)diboron to obtain 2-(4-methylaminophenyl)-6-(4,4,5,5-tetramethyl-1,3,2-dioxaborolan-2-yl) benzothiazole, wherein the boron in bis(pinacolato)diboron is $^{10}B$; and oxidizing 2-(4-methylaminophenyl)-6-(4,4,5,5-tetramethyl-1,3,2-dioxaborolan-2-yl)benzothiazole by an oxidizing agent to the compound 6-borono-2-(4-methylaminophenyl)benzothiazole of formula I, wherein the oxidizing agent may preferably be sodium metaperiodate or other oxidizing agent having a similar oxidizing ability to sodium metaperiodate.

The compound of formula I may also be prepared from the compound of formula II by the steps of:

reacting the compound 6-bromo-2-(4-nitrophenyl)benzothiazole of formula II and bis(pinacolato)diboron to obtain 2-(4-nitrophenyl)-6-(4,4,5,5-tetramethyl-1,3,2-dioxaborolan-2-yl)benzothiazole;

aoxidizing 2-(4-nitrophenyl)-6-(4,4,5,5-tetramethyl-1,3,2-dioxaborolan-2-yl)benzothiazole by an oxidizing agent to obtain 6-borono-2-(4-nitrophenyl)benzothiazole;

reducing 6-borono-2-(4-nitrophenyl)benzothiazole by a reducing agent to obtain 6-borono-2-(4-aminophenyl)benzothiazole; and reacting 6-borono-2-(4-aminophenyl)benzothiazole, methyl iodide and silver trifluoromethanesulfonate under high temperature condition to obtain the compound 6-borono-2-(4-methylaminophenyl)benzothiazole of formula I, wherein the oxidizing agent is preferably sodium metaperiodate.

In the above-mentioned two steps of synthesizing 6-borono-2-(4-methylaminophenyl)benzothiazole, the element $^{10}B$ of the compound of formula I is derived from the element $^{10}B$ of the reactant bis(pinacolato)diboron used. As described above, the content of $^{10}B$ may be adjusted as necessary.

In addition, the element C in methyl iodide may be $^{12}C$ or $^{11}C$. When the element C in the methyl iodide is $^{11}C$, 6-borono-2-(4-methylaminophenyl)benzothiazole is a compound having a radioactive element $^{11}C$. In addition to be used in elimination of amyloid β-protein in the neutron capture therapy system, this compound may also be used as a PET imaging agent for locating the location of amyloid β-protein in the brain.

When the element C in the methylamino group in the compound of formula I is $^{11}C$, since the compound of formula I has a property of specifically binding to the amyloid β-protein, the compound of formula I is labeled with $^{11}C$ and can be used to track the site of amyloid β-protein deposition in the brain by using its radioactivity in combination with Positron Emission Computed Tomography (PET) for AD diagnosis. It is to be noted that even if the compound of formula I is labeled with $^{11}C$, the compound still has a property of specifically binding to the amyloid β-protein, and the compound still contains a nuclide $^{10}B$ with large thermal neutron capture cross section, the compound of formula I labeled with $^{11}C$ still has a function for eliminating amyloid β-protein in the neutron capture therapy system.

The compound for specifically binding to the amyloid β-protein in the present disclosure is not limited to the compound of formula I, and other compounds having a nuclide with a large thermal neutron capture cross section and capable of specifically binding to amyloid β-protein are all within the scope of the present disclosure. For example, AV-45 can also specifically bind to amyloid β-protein, as is well known to those skilled in the art. The elements or functional groups of the compound are substituted with a group containing $^{10}B$ without altering its specific binding to the amyloid β-protein, it can also destroy the structure of the amyloid β-protein with the irradiation of the incident neutron beam.

An aspect of the present disclosure provides a neutron capture therapy system for eliminating amyloid β-protein using a neutron capture therapy device, and the beneficial effects of this system are targeted to efficient elimination of amyloid β-protein; Another aspect of the present disclosure also provides a compound capable of specifically binding to the amyloid β-protein for the amyloid β-protein associated with the pathogenesis of Alzheimer's disease.

Figure 4:
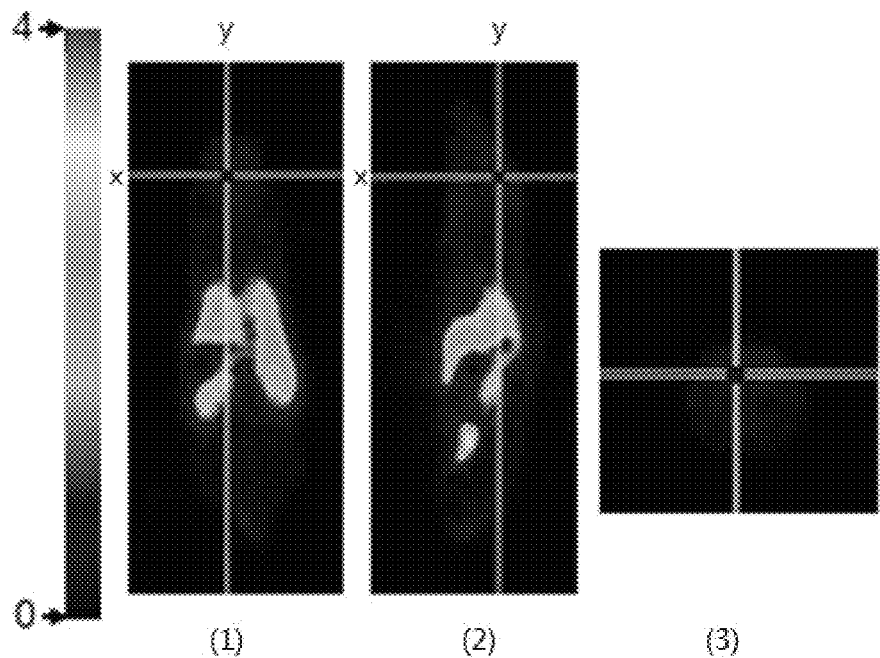
Figure 4:
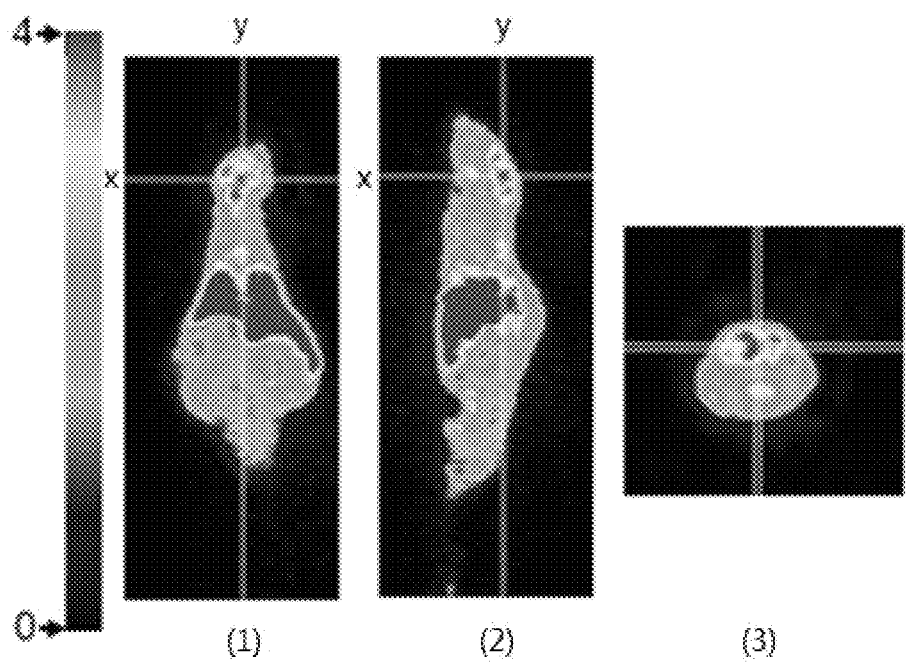

Graphs A and B in FIG. 4 are PET images of the brains of the control and SAMP8 model mice at 30 minutes after the injection of $^{11}C$ labelled 6-borono-2-(4-methylaminophenyl)benzothiazole, respectively.

Figure 5:
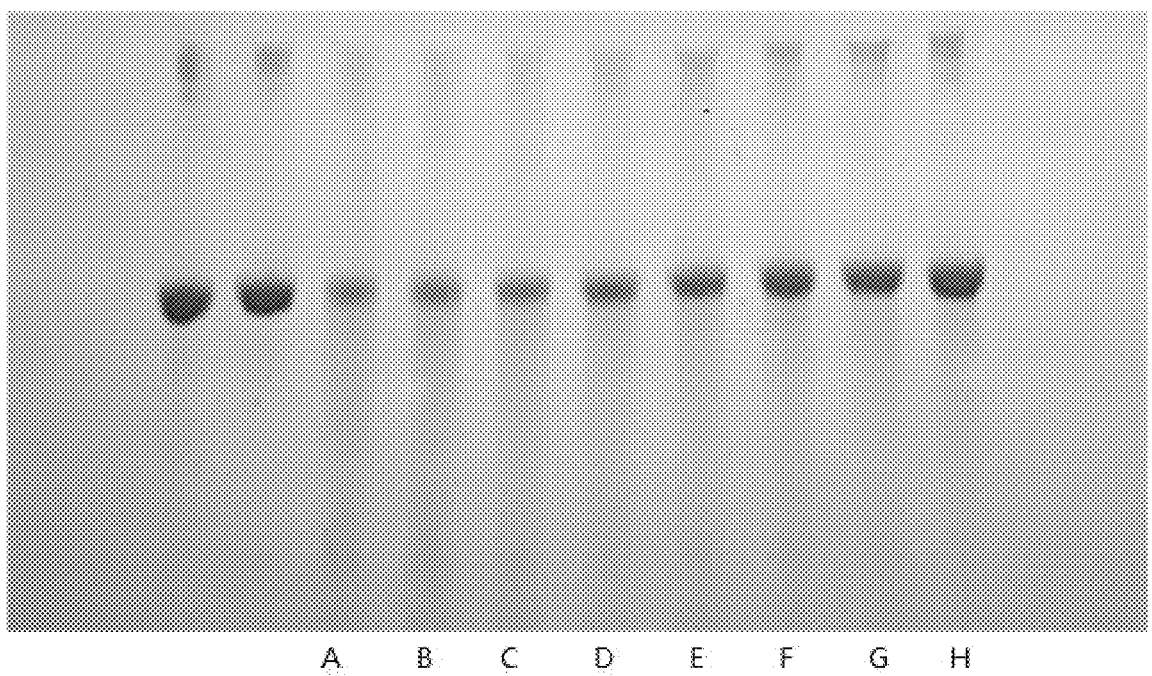

FIG. 5 is an SDS-PAGE electrophoresis pattern of BSA after exposure to different doses of radiation in $H_3{}^{10}BO_3$ at a concentration of 0.18 M.

DETAILED DESCRIPTION

The present disclosure will now be described in further detail with reference to the accompanying drawings in order to enable those skilled in the art to implement with reference to the teachings.

It is to be understood that the terms "having", "comprising", "including" as used herein do not exclude the presence or addition of one or more other ingredients or combinations thereof.

The fast neutrons herein neutrons with energy range of greater than 40 keV, epithermal neutron with energy range of 0.5 eV to 40 keV, and thermal neutron with energy range of less than 0.5 keV.

Embodiments of the present disclosure provide a neutron capture therapy system for the purpose of being able to specifically eliminate amyloid β-protein or reduce amyloid β-protein content. The system includes a neutron capture therapy device and a compound capable of specifically binding to the amyloid β-protein, which includes a nuclide with a large thermal neutron capture cross section, and commonly used nuclides are $^{10}B$, $^{155}Gd$ and $^{157}Gd$. When the thermal neutrons are irradiated to the nuclide with a large thermal neutron capture cross section, the nuclear reaction is caused, and the released energy destroys the structure of the amyloid β-protein.

Figure 1:
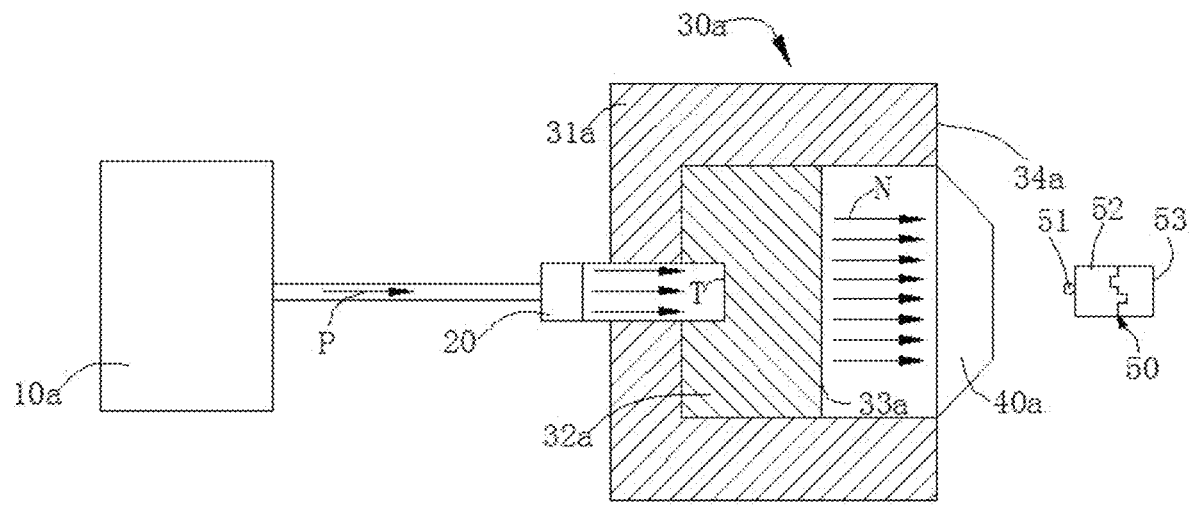
FIG. 1 is a schematic plan view of a neutron capture therapy system for an accelerator-based neutron source.
Figure 2:
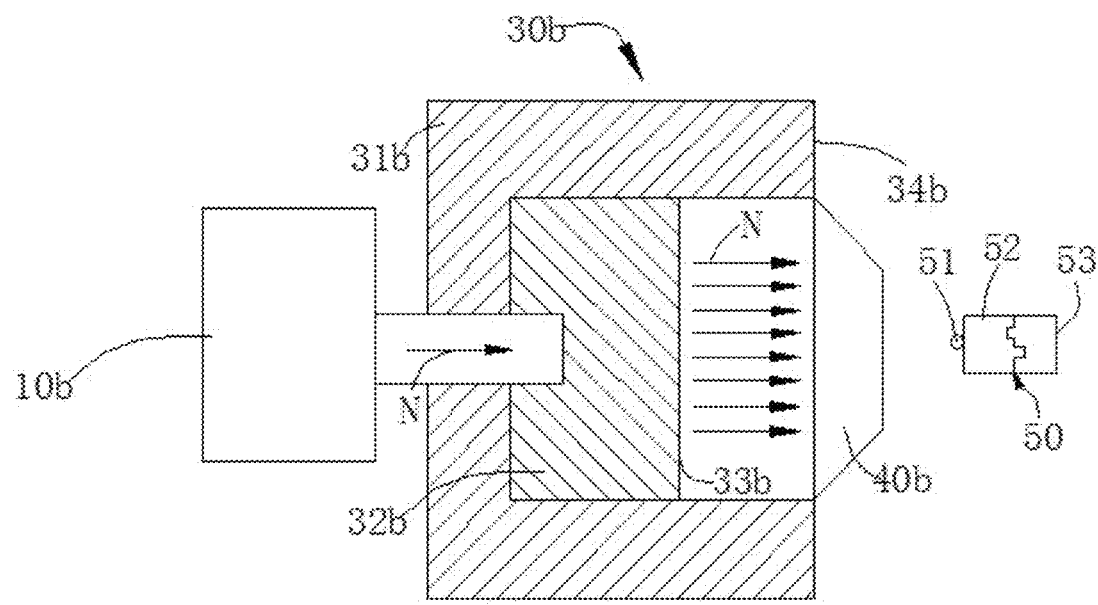
FIG. 2 is a schematic plan view of a neutron capture therapy system for a reactor-based neutron source.

As shown in FIG. 1 or FIG. 2, the neutron capture therapy device includes a neutron source, a beam shaping assembly and a collimator, wherein the beam shaping assembly includes a reflector, a moderator, a thermal neutron absorber and a radiation shielding means, wherein the neutron source includes an accelerator-based neutron source and a reactor-based neutron source.

In the practical application of the neutron capture therapy system to eliminate amyloid β-protein, it is usually necessary to adjust the fast neutrons in the mixed radiation field to the epithermal neutrons and reduce the amount of other harmful rays in the mixed radiation field in the beam shaping assembly of the neutron capture therapy device. However, considering that in the process of neutron beam travelling from the collimator of the neutron capture therapy device to a compound that specifically binds to the amyloid β-protein, the energy of the neutron beam will have a certain degree of attenuation as the distance between the two increases, and in the process for the neutron beam to arrive at the compound that specifically binds to the amyloid β-protein, there are often other substances moderating the energy of the neutrons in varying degrees, thus, in order to ensure the energy and neutron intensity of the neutrons arriving at the compound that specifically binds to the amyloid β-protein, it is usually necessary to slow the fast neutrons in the beam shaping assembly to epithermal neutrons and to increase the amount of epithermal neutrons in the neutron beam coming out of the collimator.

Referring again to FIG. 1, the neutron capture therapy device in the neutron capture therapy system is a neutron capture therapy device for the accelerator neutron source, wherein the accelerator 10a accelerates the proton, expands the cross-sectional area of the proton beam P by the beam expander 20, causes the proton beam P to hit the target T and generate neutrons. The reaction principle is that the charged particles such as proton and deuteron are accelerated by the accelerator to energy enough to overcome the target nucleus Coulomb repulsion, and carry out a nuclear reaction with the metal target T producing nuclei and neutrons, wherein, the commonly used metal targets are usually lithium and beryllium. By this method, a mixed radiation field is generated, when acting on amyloid β-protein 53 using the neutron capture therapy device, it is necessary to reduce the other kinds of rays as much as possible. And the moderator 32a in the beam shaping assembly 30a has the effect of adjusting the energy of the mixed radiation field, and the reflector 31a reflects the mixed radiation field diffused in the other direction to reduce the loss of the neutron. The beam shaping assembly 30a may also include a thermal neutron absorber 33a capable of absorbing lower energy of the thermal neutrons. The beam shaping assembly 30a is provided with a radiation shielding means 34a outside to prevent the radiation from causing damage to the nearby person. The collimator 40a is mounted at the rear of the beam shaping assembly 30a, and the beam after adjustment by the beam shaping assembly 30a is then converged by the collimator 40a to more accurately irradiate the compound 52 containing the nuclide 51 with a large thermal neutron capture cross section and capable of specifically binding to the amyloid β-protein 53. The epithermal neutron beam is more fully utilized.

Referring again to FIG. 2, the neutron capture therapy device in the neutron capture therapy system is a neutron capture therapy device for the reactor neutron source, wherein the reactor neutron source 10b passes the generated neutron beam N to the beam shaping assembly 30b through a pipe. Both the reactor neutron source 10b and the neutron source of the accelerator 10a generate a mixed radiation field. The fast neutrons having a high energy in the mixed radiation field are slowed by the moderator 32b in the beam shaping assembly 30b to neutrons that can destroy the structure of amyloid β-protein. The rays diffused in the other directions are reflected back into the moderator 32b through the reflector 31b to improve the utilization of the radiation. The thermal neutron absorber 33b in the beam shaping assembly can absorb the lower thermal neutrons in the mixed radiation field so that the epithermal neutron content in the neutron beam N is higher. The neutron beam N, after the convergence of the collimator 40b, can be used to more accurately irradiate the compound 52 containing the nuclide 51 with a large thermal neutron capture cross section and capable of specifically binding to the pathogenic protein 53. The epithermal neutron beam is more fully utilized.

The neutron capture therapy systems shown in FIGS. 1 and 2 also include a compound 52 capable of specifically binding to amyloid β-protein. The compound 52 also includes a nuclide 51 with a large thermal neutron capture cross section, and acts as an intermediate in the process of the neutron capture therapy system eliminating amyloid β-protein. First, the compound 52 is capable of recognizing and binding to the amyloid β-protein according to its nature that has a specific binding to the amyloid β-protein 53 to thereby bind the nuclide with a large thermal neutron capture cross section ($^{10}$B) 51 with amyloid β-protein 53, so that the energy generated by the reaction of the thermal neutrons and the $^{10}$B under heat neutron irradiation of the composition 50 destroys the amyloid β-protein 53.

The technical solutions of the present disclosure will be further described with reference to the following examples.

The compounds that specifically binds to amyloid β-protein described in the preferred embodiments of the present disclosure refer to 6-borono-2-(4-methylaminophenyl)benzothiazole, wherein the boron element on the compound is $^{10}$B and the compound may contain a radioactive element $^{11}$C. The boron elements in the boron-containing compounds described in the preferred embodiments of the present disclosure contain $^{10}$B, unless otherwise specified.

Example 1 Preparation of a Compound that Specifically Binds to Amyloid β-Protein The compound 6-borono-2-(4-methylaminophenyl)benzothiazole of the formula I can be prepared by steps of:

formula I

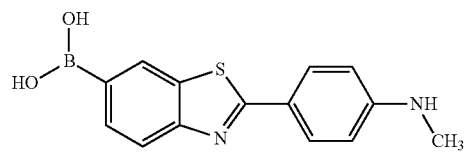

1 g of 6-bromo-2-(4-nitrophenyl)benzothiazole was dissolved in 10 mL of ethanol and 5.39 g of $SnCl_2.2H_2O$ was added. The reaction was stirred at 100° C. for 1 h to obtain 6-bromo-2-(4-aminophenyl)benzothiazole;

$^1$H NMR: 400 MHz DMSO

δ 8.29 (s, 1H), 7.80-7.82 (d, J=8.8 Hz, 1H), 7.74-7.76 (d, J=8.8 Hz, 2H), 7.58-7.60 (m, 1H), 6.65-6.67 (d, J=8.4 Hz, 2H), 5.95 (s, 2H).

To 1 g of 6-bromo-2-(4-aminophenyl)benzothiazole was added 16.4 mmol of formaldehyde, 10 mL of tetrahydrofuran (THF) and 20 mL of methanol were added thereto, and 0.886 g of sodium methoxide was added in one portion, and the reaction solution was stirred at 65° C. for 12 h, and then was cooled to 25° C., 620.41 mg of sodium borohydride ($NaBH_4$) was added and the reaction temperature was raised to 65° C. The reaction was stirred for 1 h to obtain 6-bromo-2-(4-methylaminophenyl)benzothiazole;

$^1$H NMR: 400 MHz $CDCl_3$

δ 7.97 (s, 1H), 7.89-7.91 (d, J=8.8 Hz, 2H), 7.81-7.83 (d, J=8.8 Hz, 1H), 7.52-7.54 (m, 1H), 6.64-6.66 (d, J=8.8 Hz, 2H), 2.93 (s, 3H).

Figure 3:
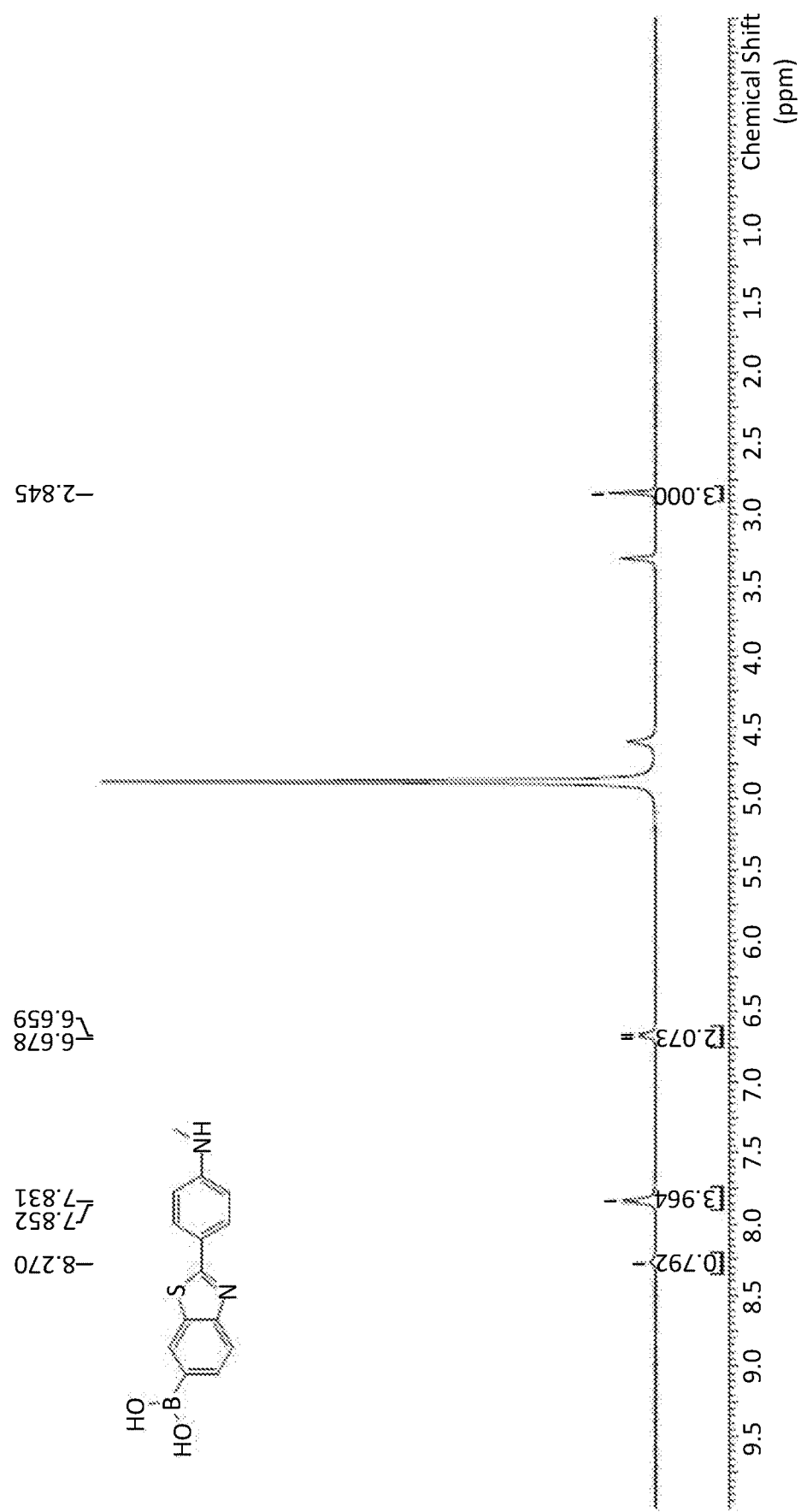
FIG. 3 is a $^1H$ NMR spectrum of a compound (6-borono-2-(4-methylaminophenyl)benzothiazole) that specifically binds to amyloid β-protein.

A reaction system consisted of 100 mg of 6-bromo-2-(4-methylaminophenyl)benzothiazole, 95.46 mg of bis(pinacolato)diboron and 92.23 mg of potassium acetate. To the reaction system was added 4 mL of THF and 2 mL of dimethylsulfoxide (DMSO). 26.39 mg of dichlorobis (triphenylphosphine) palladium ($Pd(PPh_3)_2Cl_2$) was added under nitrogen at 20° C. and the reaction was stirred at 90° C. for 12 h to obtain 2-(4-methylaminophenyl)-6-(4,4,5,5-tetramethyl-1,3,2-dioxaborolan-2-yl)benzothiazole, wherein the boron in the bis(pinacolato)diboron includes $^{10}B$;

300 mg of 2-(4-methylaminophenyl)-6-(4,4,5,5-tetramethyl-1,3,2-dioxaborolan-2-yl)benzothiazole was added to 20 mL of THF and 10 mL of water, and then 875.93 mg of sodium metaperiodate ($NaIO_4$) was added to form a reaction system. The reaction system was stirred at 25° C. for 12 h to obtain the compound of formula I: 6-borono-2-(4-methylaminophenyl)benzothiazole. The $^1H$ NMR scan spectrum of the compound is shown in FIG. 3.

$^1H$ NMR: 400 MHz MeOH

δ 8.27 (s, 1H), 7.83-7.85 (m, 4H), 6.66-6.68 (d, J=7.6 Hz, 2H), 2.85 (s, 3H).

Wherein, 6-bromo-2-(4-nitrophenyl)benzothiazole can be prepared by the steps of:

5 g of 6-bromo-2-amino-benzothiazole was added to 25 mL of a solution of potassium hydroxide at a concentration of 10M, and then 5 mL of ethylene glycol was added to form a mixed solution which was stirred at 125° C. for 2 h to obtain 2-amino-bromophenyl mercaptan;

$^1H$ NMR: 400 MHz DMSO

δ 7.21-7.26 (m, 1H), 6.99 (s, 1H), 6.81-6.72 (m, 1H), 6.39 (s, 1H), 5.72 (s, 2H).

1.48 g of p-nitrobenzaldehyde was added to 2 g of 2-amino-5-bromophenyl mercaptan, and then 40 mL of DMSO was added to form a reaction solution, which was stirred at 180° C. for 0.5 h to obtain 6-bromo-2-(4-nitrophenyl)benzothiazole;

$^1H$ NMR: 400 MHz DMSO

δ 8.54 (s, 1H), 8.34-8.41 (m, 4H), 8.07-8.09 (d, J=8.8 Hz, 1H), 7.74-7.77 (m, 1H).

The specific reaction procedure for the synthesis of 6-borono-2-(4-methylaminophenyl)benzothiazole in this example is shown in Scheme II (The boron element in the scheme includes $^{10}B$):

Scheme II

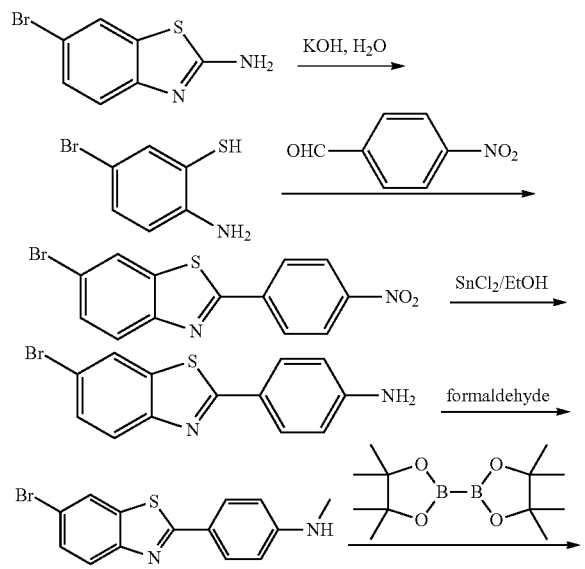

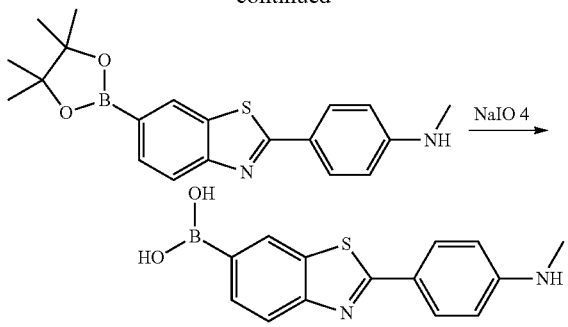

Example 2 Preparation of a Compound that Specifically Binds to Amyloid β-Protein The synthesis method of 6-bromo-2-(4-nitrophenyl)benzothiazole in this example is the same as that shown in Example 1.

To 100 mg of 6-bromo-2-(4-nitrophenyl)benzothiazole was added 90.91 mg of bis(pinacolato)diboron and 87.84 mg of potassium acetate, then, 4 mL of THF and 2 mL of DMSO was added, and 25 mg of dichlorobis (triphenylphosphine) palladium was added under nitrogen at 20° C., and the reaction system was stirred at 95° C. for 15 h to obtain 2-(4-nitrophenyl)-6-(4,4,5,5-tetramethyl-1,3,2-dioxaborolan-2-yl)benzothiazole, wherein the boron in the bis(pinacolato)diboron includes $^{10}B$ $^1H$ NMR: 400 MHz $CDCl_3$ δ 8.44 (s, 1H), 8.35-8.37 (d, J=8.8 Hz, 2H), 8.28-8.30 (d, J=8.8 Hz, 2H), 8.11-8.13 (d, J=8 Hz, 1H), 7.96-7.98 (d, J=8 Hz, 1H), 1.40 (s, 12H).

To 539.7 mg of 2-(4-nitrophenyl)-6-(4,4,5,5-tetramethyl-1,3,2-dioxaborolan-2-yl)benzothiazole was added 30 mL of THF and 10 mL of water, followed by the addition of 1.51 g of sodium metaperiodate, the reaction system was reacted at 25° C. for 23 h to obtain 6-borono-2-(4-nitrophenyl)benzothiazole;

$^1H$ NMR: 400 MHz DMSO

δ 8.56 (s, 1H), 8.36-8.42 (m, 4H), 8.29 (m, 2H), 8.10-8.12 (d, J=8.4 Hz, 1H), 8.00 (m, 1H).

To 100 mL of methanol was added 200 mg of catalyst Pd/C, and then 180 mg of 6-borono-2-(4-nitrophenyl)benzothiazole was added to form a reaction system, the reaction system was vacuum degassed in a hydrogen atmosphere and reacted at 25° C. for 10 min to obtain 6-borono-2-(4-aminophenyl)benzothiazole;

$^1H$ NMR: 400 MHz MeOH

δ 8.29 (s, 1H), 7.80-7.84 (m, 4H), 6.74-6.76 (d, J=8.8 Hz, 2H).

Methyl iodide was carried by nitrogen to pass through a silver trifluoromethanesulfonate tube heated to 200° C., and then passed into anhydrous acetone in which 6-borono-2-(4-aminophenyl)benzothiazole was dissolved to form a reaction solution, the reaction solution was reacted at 80° C. for 5 min and quenched with water to obtain 6-borono-2-(4-methylaminophenyl)benzothiazole.

Wherein C in the methyl iodide may be a radioactive $^{11}C$, thus, 6-borono-2-(4-methylaminophenyl)benzothiazole synthesized from it also has a radioactive element $^{11}C$, therefore, the radioactive compound can be used in conjunction with PET to track the site of amyloid β-protein deposition in the brain and the diagnosis of AD.

$^1H$ NMR: 400 MHz MeOH

δ 8.27 (s, 1H), 7.83-7.85 (m, 4H), 6.66-6.68 (d, J=7.6 Hz, 2H), 2.85 (s, 3H).

Wherein C in the methyl iodide may be a radioactive $^{11}C$, thus, 6-borono-2-(4-methylaminophenyl)benzothiazole synthesized from it also has a radioactive element $^{11}C$, therefore, the radioactive compound can be used in conjunction with Micro-PET to track the site of amyloid β-protein deposition in the brain and the diagnosis of AD.

The reaction procedure of this example is shown in Scheme III (The boron element in the scheme includes $^{10}B$):

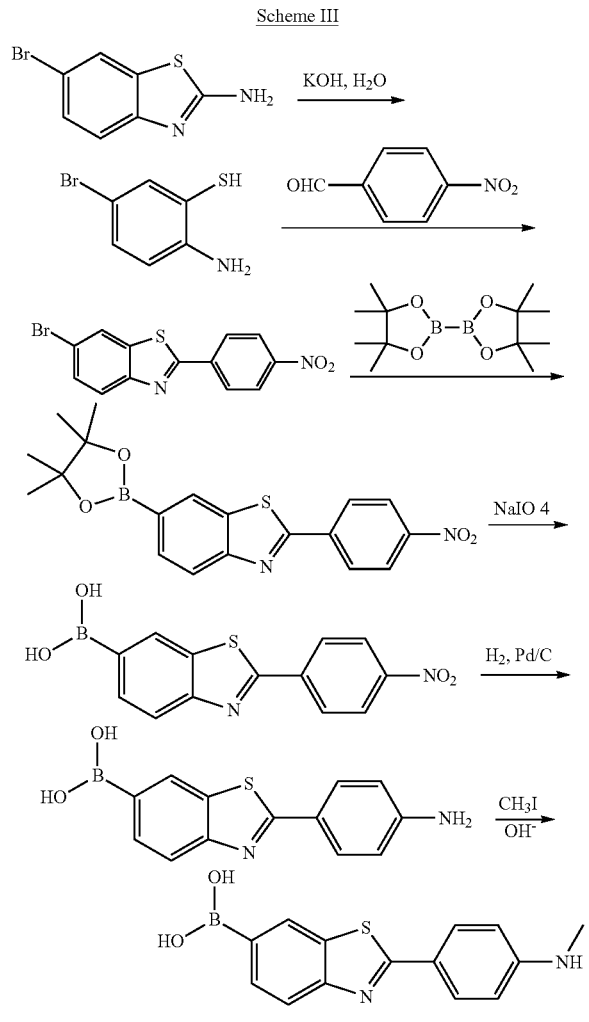

Scheme III

Example 3 Experiment of $^{11}C$-Labeled 6-borono-2-(4-methylaminophenyl)benzothiazole Specifically Binding to Amyloid β-Protein SAMP8 (senescence accelerated mouse prone 8) mice are the most common animal model of AD (Alzheimer's disease), in its brain there are a large number of amyloid deposition plaque. In this example, SAMP8 mice were used as model mice, and the normal mice were used as the control mice. Both the model mice and the control mice were 10 months old. The two mice were injected with 6-borono-2-(4-methylaminophenyl)benzothiazole containing $^{11}C$ labeling, and the Micro-PET scan is used to study whether 6-borono-2-(4-methylaminophenyl)benzothiazole and amyloid β-protein have specific binding properties. Model mice and control mice weighing 31.5±0.3 g were selected, 31.0±0.6 μCi of $^{11}C$ labelled 6-borono-2-(4-methylaminophenyl)benzothiazole were injected thereto, and Micro-PET of Model INVEON from Siemens were used for scan, where the scanning window was 350-650 KeV.

It is well known to those skilled in the art that the major cause of Alzheimer's disease is that the amyloid β-protein deposition plaques accumulate in the cerebral cortex and hippocampus of the brain. In this example, Micro-PET scanned and compared the brains of the model and control mice using PMOD software. And the absorption of radioactive 6-borono-2-(4-methylaminophenyl)benzothiazole in the cerebral cortex and hippocampus of SAMP8 model mice and control mice was determined, to further illustrate that the compound is capable of specifically binding to amyloid β-protein deposition plaques. The specific results are shown in Table 1 and Table 2:

TABLE 1

The uptake of radioactive 6-borono-2-(4-methylaminophenyl)benzothiazole in cerebral cortex of model mice and control mice

| Time after radiopharmaceutical injection (min) | Cerebral cortex uptake of radiopharmaceuticals(% ID/g) | | Ratio (model mice/control mice) |
|---|---|---|---|
| | Model mice | Control mice | |
| 5 | 3.03 | 1.61 | 1.9 |
| 15 | 2.88 | 1.48 | 1.9 |
| 25 | 2.79 | 1.17 | 2.4 |
| 35 | 2.68 | 0.99 | 2.7 |

As can be seen from Table 1: 35 minutes after the injection of radiopharmaceuticals, the cerebral cortex uptake ratio of the model mice to the control mice was 2.7, higher than the boron ratio (2.5) of the target and the non-target in the effective boron neutron capture therapy. The results suggest that radioactive 6-borono-2-(4-methylaminophenyl) benzothiazole can be effectively bound to the amyloid β-protein deposition plaque and accumulate at the lesion. It is more desirable for the patients with Alzheimer's disease treated with boron neutron capture therapy, the lesions can accept a large number of radiation dose, to achieve the purpose of treatment, and reduce the radiation damage to the normal brain tissue.

TABLE 2

The uptake of radioactive 6-borono-2-(4-methylaminophenyl)benzothiazole in hippocampus of model mice and control mice

| Time after radiopharmaceutical injection (min) | hippocampus uptake of radiopharmaceuticals(% ID/g) | | Ratio (model mice/control mice) |
|---|---|---|---|
| | Model mice | Control mice | |
| 5 | 3.44 | 1.80 | 1.9 |
| 15 | 3.50 | 1.49 | 2.3 |
| 25 | 3.45 | 1.09 | 3.2 |
| 35 | 3.27 | 1.01 | 3.2 |

As can be seen from Table 2, 25 and 35 minutes after the injection of radiopharmaceuticals, the hippocampus ratio of the model mice to the control mice was 3.2, higher than the boron ratio (2.5) of the target and the non-target in the effective boron neutron capture therapy. The results also suggest that radioactive 6-borono-2-(4-methylaminophenyl) benzothiazole can be effectively bound to the amyloid β-protein deposition plaque and accumulate at the lesion.

SAMP8 model mice are accelerated aging mice with Alzheimer's disease, and a large number of amyloid β-protein deposition plaque are accumulated in the cerebral cortex and hippocampus lesions. It can be seen from the experimental data of the model mice and the control mice in Table 1 and Table 2 that the cerebral cortex and hippocampus of the SAMP8 model mice have a stronger ability to absorb 6-borono-2-(4-methylaminophenyl)benzothiazole compared to the normal control mice. It is also further explained that 6-borono-2-(4-methylaminophenyl)benzothiazole is specific for amyloid β-protein are specific, and boron neutron capture therapy can be used in the future to treat Alzheimer's disease and provide another advanced treatment for patients with Alzheimer's disease.

According to the results of the analysis of Table 2, 25 to 35 minutes after the injection of radioactive 6-borono-2-(4-methylaminophenyl)benzothiazole in mice, the ratio of radiopharmaceuticals in the hippocampus of the model mice and mice was 3.2. Thus, the Micro-PET image of the intermediate value of 30 minutes was used to further compare the accumulation of the radioactivity of 6-borono-2-(4-methylaminophenyl)benzothiazole in the brain.

FIG. 4 is an image of PET scan and processed by AMIDE software at 30 min after the injection of radioactive 6-borono-2-(4-methylaminophenyl)benzothiazole, wherein graph A is the image of the control mice injected with radiopharmaceutical at 30 min, in graph A, picture (1) shows the scan image of coronal section of the control mouse, picture (2) is a cross-sectional view of picture (1) along the Y-axis, picture (3) is a brain cross-sectional view of picture (1) along the Y-axis; graph B is the image of the SAMP8 model mice injected with radiopharmaceutical at 30 min, similarly, in graph B, picture (1) shows the scan image of coronal section of the control mouse, picture (2) is a cross-sectional view of picture (1) along the Y-axis, picture (3) is a brain cross-sectional view of picture (1) along the Y-axis Wherein picture (3) of graph A and picture (3) of graph B can reflect the brain radiopharmaceutical absorption. It can be seen from comparison of these two images, the brain of the SAMP8 model mouse in graph B (3) has accumulated a large amount of radiopharmaceuticals relative to the brain of the control mice in graph A (3), and it is already known that the model mouse brain has a large number of amyloid β-protein deposition plaques, it can be explained that 6-borono-2-(4-methylaminophenyl)benzothiazole is specific for amyloid β-protein deposition plaque, and in the future 6-borono-2-(4-methylaminophenyl)benzothiazole can be used for boron neutron capture therapy.

Example 4 Experiment for Simulation of the Neutron Capture Therapy System to Eliminate Protein In this example, boronic acid ($H_3{}^{10}BO_3$) was used in place of 6-borono-2-(4-methylaminophenyl)benzothiazole, wherein the boron element in boric acid ($H_3{}^{10}BO_3$) was $^{10}B$, and bovine serum albumin (BSA) was used to mimic amyloid β-protein. The mixed solution of boric acid and bovine serum albumin was placed in a neutron beam capture environment. The effect of neutron on bovine serum albumin and the effect of neutron on bovine serum albumin in the presence of $H_3{}^{10}BO_3$ were analyzed by SDS-PAGE gel electrophoresis.

I. Effect of Neutron on Bovine Serum Albumin

A BSA solution of concentration of 0.01% (w/w) was prepared with ultrapure water, and the prepared solution was stored and operated at 4° C. A 1 mL BSA solution was placed on the centerline of the exit of the collimator of the neutron capture therapy device, wherein the distance of the solution from the exit of the collimator was 2 cm and a neutron capture therapy device was arranged so that the neutron intensity at the exit of the collimator was $2.4*10^{11}$/s, and the BSA solution was irradiated in the neutron environment for 2 h; another 1 mL BSA solution was taken as a control solution without neutron irradiation.

The BSA solution with neutron irradiation for 2 h and the control solution were stained with Coomassie brilliant blue and subjected to SDS-PAGE gel electrophoresis, the colors of the protein bands in the electrophoresis pattern of the sample solution and the control solution were quantified by Image J software, and the values were used to represent the relative content of protein, wherein the content of BSA in the control solution was defined as 1. Under the above neutron irradiation experiment, the content of BSA after the neutron irradiation for 2 h was 0.8, and its content was reduced by about 20%. It can be seen that the radiation containing the neutron beam can affect the protein content.

II. Effect of Neutron on Bovine Serum Albumin in the Presence of $H_3{}^{10}BO_3$ A solution of BSA and $H_3{}^{10}BO_3$ was prepared with ultrapure water, wherein in the solution, the concentration of BSA was 0.01% (w/w), and the concentration of $H_3{}^{10}BO_3$ was 0.18 M; and the prepared solution was stored and operated at 4° C. 8 parts (numbered A, B, C, D, E, F, G, H, respectively) were taken from the solution, and 1 mL of each solution was irradiated with a neutron capture therapy device. 8 parts of the solution were respectively placed on the center line of the exit of the collimator of the neutron capture therapy device, Solution A was 2 cm from the exit of the collimator, Solution B was 4 cm from the exit of the collimator, Solution C was 6 cm from the exit of the collimator, and so on. The beam at the exit of the collimator, in addition to the neutron beam, also includes gamma rays and other radiation, mainly neutron rays that actually destroy the protein. The example described the intensity of the beam with the neutron intensity in the beam, wherein, the neutron strength used in the present example was $2.4*10^{11}$/s, and 8 parts of the solution were irradiated for 2 h in the neutron environment; and another 1 mL of the BSA and $H_3{}^{10}BO_3$ solution was used as a control solution without neutron irradiation.

The control solution and the 8 parts of the solution irradiated by the radiation of the neutron capture therapy device were stained with Coomassie Brilliant Blue and subjected to SDS-PAGE gel electrophoresis. FIG. 5 shows the SDS-PAGE electrophoresis pattern of the control solution and the 8 parts of the solution.

The first two protein bands in FIG. 5 were BSA in the control solution and the rest were BSA after exposure to the radiation. 8 parts of the solution were placed on the center line of the exit of the collimator. Since the solutions on the center line all contain $H_3{}^{10}BO_3$ and the $^{10}B$ element has a large thermal neutron capture cross section, the neutron dose decreased significantly after the neutrons in the radiation from the exit of the collimator were passed through the solution containing $H_3{}^{10}BO_3$. The farther away from the collimator, the less the neutron radiation dose received by the BSA.

As can be seen from FIG. 5, the colors of the protein bands of the eight neutron-irradiated solution became lighter in different degrees compared to that of the control. And the closer to the exit of the collimator, the lighter the color of the protein bands in the solutions, indicating the more the protein content was reduced, and the closer to the exit of the collimator, the greater the neutron radiation dose received by the solution. It is further explained that the size of the neutron dose affects the content of BSA in the solution, and the stronger the neutron dose, the less the content of BSA in the solution after the neutron irradiation.

The colors of the BSA protein bands in the electrophoresis patterns corresponding to the control solution and 8 parts of the solution were quantified by Image J software, and the values were used to represent the relative content of the protein, wherein the content of BSA in the control solution was defined as 1. Under the above neutron irradiation experiment, the contents of BSA after neutron irradiation for 2 h are shown in Table 3.

It can be seen from Table 3, the content of BSA in the solution irradiated by neutrons decreased to varying degrees. After 2 hours of neutron irradiation with a neutron intensity of $2.4*10^{11}$/s on the solution placed at 2 cm from the exit of the collimator, the BSA content thereof was only 5.3%, indicating that the neutron can greatly destroy the structure of BSA and decrease the content of BSA in the presence of $H_3{}^{10}BO_3$. And within the allowable range of experimental error, among the 8 solutions, the farther distance of the solution from the exit of the collimator, the BSA contents as a whole showed a decreasing trend, further indicating that the size of the neutron dose affected the BSA content.

TABLE 3 effect of neutron on bovine serum albumin in the presence of $H_3{}^{10}BO_3$

| Solution number | BSA content (%) |
|---|---|
| Control solution | 100 |
| A | 5.3 |
| B | 2.6 |
| C | 18.9 |
| D | 14.0 |
| E | 22.9 |
| F | 35.1 |
| G | 49.6 |
| H | 60.7 |

The compound 6-borono-2-(4-methylaminophenyl)benzothiazole provided by the present disclosure carry a nuclide $^{10}B$ with a large thermal neutron capture cross section as $H_3{}^{10}BO_3$ and capable of specifically binding to the amyloid β-protein. The compound is placed in an environment containing amyloid β-protein, and the compound will form a high concentration around the amyloid β-protein. Then the region where the compound accumulates is irradiated with neutron beam emitted by a neutron capture therapy device, and the energy released can destroy the structure of the protein.

While the present disclosure has been described in detail with reference to specific embodiments thereof, it is to be noted that the above embodiments are provided for the purpose of further explanation of the disclosure and are not representative of the scope of the disclosure, that non-essential modifications and adjustment made by others in accordance with the teachings of the present disclosure is still within the scope of the present disclosure.

What is claimed is:

1. A neutron capture therapy system for eliminating amyloid β-protein, comprising:
   a neutron capture therapy device, and
   a compound for specifically binding to the amyloid β-protein,
   wherein the compound contains a nuclide with a large thermal neutron capture cross section; and wherein the energy generated by the action of a neutron beam generated by the neutron capture therapy device on the nuclide of the compound destroys the structure of the amyloid β-protein, and
   wherein the compound for specifically binding to the amyloid β-protein has a structure of formula I:

formula I

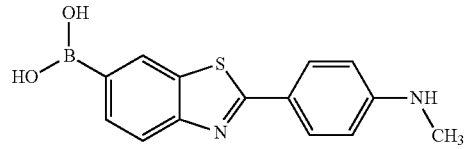

wherein B in the B(OH)$_2$-group of the formula I is $^{10}B$.

2. The neutron capture therapy system for eliminating amyloid β-protein according to claim 1, wherein the nuclide with a large thermal neutron capture cross section is elected from the group consisting of $^{10}B$, $^{155}Gd$, and $^{157}Gd$, wherein the neutron beam generated by the neutron capture therapy device undergoes a boron neutron capture reaction with the nuclide $^{10}B$ in the compound to destroy the structure of the amyloid β-protein by the two heavy particles of $^4He$ and $^7Li$ produced.

3. The neutron capture therapy system for eliminating amyloid β-protein according to claim 1, wherein the neutron capture therapy device comprises:
   a neutron source for generating a neutron beam;
   a beam shaping assembly located at the rear of the neutron source for shifting fast neutrons in the neutron beam with a wider spectrum generated by the neutron source to epithermal neutrons or thermal neutrons; and
   a collimator located at the rear of the beam shaping assembly for converging the epithermal neutrons or the thermal neutrons.

4. The neutron capture therapy system for eliminating amyloid β-protein according to claim 3, wherein the neutron source is an accelerator-based neutron source or a reactor-based neutron source.

5. The neutron capture therapy system for eliminating amyloid β-protein according to claim 3, wherein the beam shaping assembly comprises:
   a moderator for moderating fast neutrons into epithermal neutrons or thermal neutrons; and
   a reflector surrounding the moderator for reflecting neutrons diffused outside the beam shaping assembly back into the moderator.

6. The neutron capture therapy system for eliminating amyloid β-protein according to claim 1, wherein the compound of formula I is prepared from a compound of formula II:

formula II

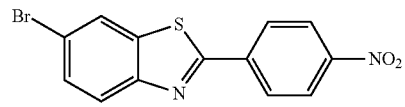

the compound of formula II is 6-bromo-2-(4-nitrophenyl)benzothiazole.

7. The neutron capture therapy system for eliminating amyloid β-protein according to claim 6, wherein a process for preparing the compound of formula I from the compound of formula II comprises steps of:

reducing the compound of formula II to obtain 6-bromo-2-(4-aminophenyl)benzothiazole;

reacting 6-bromo-2-(4-aminophenyl)benzothiazole and formaldehyde to obtain 6-bromo-2-(4-methylaminophenyl)benzothiazole;

reacting 6-bromo-2-(4-methylaminophenyl)benzothiazole and bis(pinacolato)diboron to obtain 2-(4-methylaminophenyl)-6-(4,4,5,5-tetramethyl-1,3,2-dioxaborolan-2-yl)benzothiazole; and oxidizing 2-(4-methylaminophenyl)-6-(4,4,5,5-tetramethyl-1,3,2-dioxaborolan-2-yl)benzothiazole by an oxidizing agent to the compound 6-borono-2-(4-methylaminophenyl)benzothiazole of formula I;

wherein the boron in bis(pinacolato)diboron is $^{10}$B.

8. The neutron capture therapy system for eliminating amyloid β-protein according to claim 6, wherein a process for preparing the compound of formula I from the compound of formula II comprises steps of:

reacting the compound of formula II and bis(pinacolato)diboron to obtain 2-(4-nitrophenyl)-6-(4,4,5,5-tetramethyl-1,3,2-dioxaborolan-2-yl)benzothiazole;

oxidizing 2-(4-nitrophenyl)-6-(4,4,5,5-tetramethyl-1,3,2-dioxaborolan-2-yl)benzothiazole by an oxidizing agent to obtain 6-borono-2-(4-nitrophenyl)-6-benzothiazole;

reducing 6-borono-2-(4-nitrophenyl)benzothiazole by a reducing agent to obtain 6-borono-2-(4-aminophenyl)benzothiazole; and reacting 6-borono-2-(4-aminophenyl)benzothiazole, methyl iodide and silver trifluoromethanesulfonate to obtain the compound 6-borono-2-(methylaminophenyl)benzothiazole of formula I;

wherein the boron in bis(pinacolato)diboron is $^{10}$B.

9. The neutron capture therapy system for eliminating amyloid β-protein according to claim 8, wherein C in the methyl iodide is $^{11}$C.

* * * * *